United States Patent [19]

Hamberger et al.

[11] Patent Number: 4,680,291

[45] Date of Patent: Jul. 14, 1987

[54] PROPENYLAMINES, PROCESSES FOR THEIR PRODUCTION AND PHARMACEUTICAL COMPOSITIONS CONTAINING THEM

[75] Inventors: Helmut Hamberger; Adrian Stephen, both of Vienna; Anton Stütz, Maria Enzersdorf; Peter Stütz, Vienna, all of Austria

[73] Assignee: Sandoz Ltd., Basel, Switzerland

[21] Appl. No.: 934,772

[22] Filed: Aug. 18, 1978

[30] Foreign Application Priority Data

| Aug. 19, 1977 | [CH] | Switzerland | 10203 |
| Aug. 19, 1977 | [CH] | Switzerland | 10202 |
| Oct. 24, 1977 | [SE] | Sweden | 12909 |
| Oct. 24, 1977 | [CH] | Switzerland | 12910 |

[51] Int. Cl.$^4$ .......................... R61K 31/135

[52] U.S. Cl. .................... 514/183; 514/187; 514/255; 514/269; 514/315; 514/649; 546/152; 546/184; 546/348; 549/29; 549/49; 564/387; 568/425

[58] Field of Search ............ 260/570.9; 424/330; 564/387

[56] References Cited

U.S. PATENT DOCUMENTS

| 2,601,275 | 6/1952 | Gump et al. | 564/386 X |
| 3,320,277 | 5/1967 | Mehta et al. | 564/391 X |
| 3,784,642 | 1/1974 | Jenny et al. | 564/387 X |
| 4,139,560 | 2/1979 | Reinehr et al. | 564/384 |
| 4,282,251 | 8/1981 | Berney | 564/387 X |

*Primary Examiner*—Robert V. Hines
*Attorney, Agent, or Firm*—Gerald D. Sharkin; Robert S. Honor; Thomas O. McGovern

[57] ABSTRACT

The present invention provides propenylamines useful as anti-mycotic agents.

42 Claims, No Drawings

PROPENYLAMINES, PROCESSES FOR THEIR PRODUCTION AND PHARMACEUTICAL COMPOSITIONS CONTAINING THEM

This invention relates to propenyl-amines, processes for their production and pharmaceutical compositions containing them.

The present invention provides a compound of formula I,

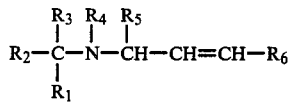

I wherein
(a)
(i) $R_1$ is a radical of formula IIa,

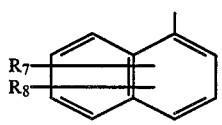

IIa wherein
$R_7$ and $R_8$, independently, are hydrogen, halogen of atomic number from 9 to 53, trifluoromethyl, hydroxy, nitro, lower alkyl or lower alkoxy, or a radical of formula IIb, IIc, IId, IIe,

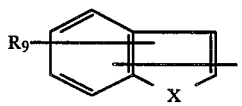

IIb

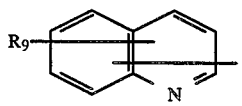

IIc

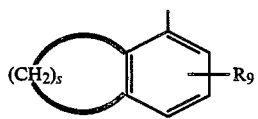

IId

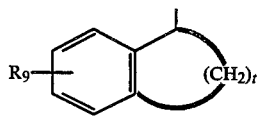

IIe wherein
$R_9$ is hydrogen, halogen of atomic number from 9 to 53, hydroxy, lower alkyl or lower alkoxy,
X is oxygen, sulpher, imino, lower alkylimino or a radical of formula —(CH$_2$)$_r$— wherein r is 1, 2, or 3,
s is 3, 4 or 5, and
t is 2, 3 or 4, and
$R_2$ is hydrogen or lower alkyl, or
(ii) $R_1$ and $R_2$ together with the carbon atom to which they are bound form a radical of formula IIf or IIg,

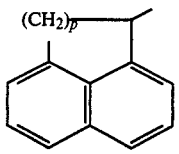

IIf

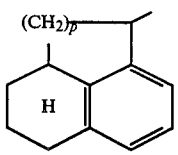

IIg wherein
p is 1, 2 or 3,
$R_3$ and $R_5$, independently, are hydrogen or lower alkyl,
$R_4$ is alkyl ($C_{1-6}$), alkenyl ($C_{3-12}$), alkynyl ($C_{3-12}$) or cycloalkyl ($C_{3-8}$), alkyl ($C_{1-6}$); and
$R_6$ is (i) an aromatic, five-membered heterocycle containing one oxygen, sulpher or nitrogen hetero-ring atom and optionally an additional one or two nitrogen hetero-ring atoms and being optionally substituted on a carbon ring atom by halogen of atomic number from 9 to 53, hydroxy, lower alkyl or lower alkoxy, and any nitrogen ring atom present being optionally substituted when possible, by lower alkyl, (ii) a radical of formula IIIa,

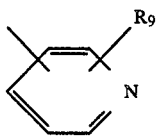

IIIa wherein
$R_9$ is defined above,
(iii) a radical of formula IIIb,

—CO—$R_{10}$   IIIb wherein
$R_{10}$ is alkyl ($C_{1-12}$), alkenyl ($C_{3-12}$), alkynyl ($C_{3-12}$) cycloalkyl ($C_{3-8}$), alkyl ($C_{1-6}$), phenyl-alkyl ($C_{7-12}$), phenyl, phenylalkoxy ($C_{7-16}$), or aminoalkyl ($C_{1-12}$);
(iv) a radical of formula IIIc, IIId or IIIe,

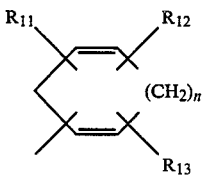

IIIc

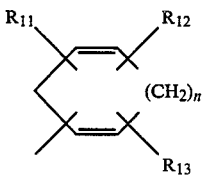

IIId

-continued

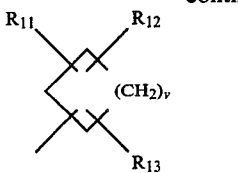
IIIe wherein
$R_{11}$, $R_{12}$ and $R_{13}$, independently, are hydrogen or lower alkyl,
m is a whole number from 0 to 4,
n is a whole number from 0 to 3, and
v is a whole number from 0 to 5,
(v) a radical of formula IIIf,

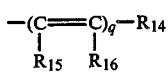

wherein
$R_{14}$ is lower alkyl, alkoxy ($C_{1-12}$), carbonyl, alkenyl ($C_{3-12}$), alkynyl ($C_{3-12}$), phenylalkyl ($C_{7-12}$) or phenyl,
$R_{15}$ and $R_{16}$, independently, are hydrogen or lower alkyl, and
q is a whole number from 0 to 5, or
(vi) a radical of formula IIIg

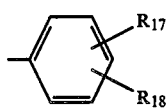
IIIg wherein
$R_{17}$ and $R_{18}$, independently, are hydrogen, halogen of atomic number from 9 to 53, trifluoromethyl, hydroxy, nitro, lower alkyl or lower alkoxy, with the proviso that one of $R_{17}$ and $R_{18}$ is other than hydrogen, and with the general proviso that $R_1$ is not a radical of formula IIa when $R_6$ is a radical of formula IIIg or phenyl, $R_2$ is hydrogen and $R_3$ is hydrogen or lower alkyl,
(b)
$R_1$ is a radical of formula IIa to IIe, as defined above,
$R_2$, $R_5$ and $R_6$ are as defined above, and $R_3$ and $R_4$ together are —(CH$_2$)$_u$— wherein u is a whole number from 1 to 8.

Any lower alkyl or lower alkoxy radical has preferably 1 to 4 carbon atoms, especially 2 or 1 carbon atoms. Any alkyl ($C_{1-12}$) moiety is preferably alkyl ($C_{2-8}$); phenylalkyl or phenylalkoxy has preferably 7 carbon atoms. Any alkenyl or alkynyl radical has preferably 3 to 6 carbon atoms, especially 3 to 4 carbon atoms. Preferably the multiple bond is in other than the α, β position and is conveniently in the remote terminal position. An example of an alkenyl group is allyl. An example of an alkynyl group is propinyl, Cycloalkylalkyl has preferably an alkyl moiety of 1 to 4 carbon atoms, especially 2 or 1 carbon atoms, and a cycloalkyl moiety preferably of 3 to 6 carbon atoms. When $R_4$ is cycloalkylalkyl this is especially cyclopentyl alkyl or cyclohexylalkyl. When $R_{10}$ is cycloalkylalkyl this is especially cyclopropylalkyl or cyclobutylalkyl.

Conveniently $R_7$ and $R_8$ are identical and are both hydrogen. Conveniently $R_9$ is hydrogen or halogen. In IIb and IIc the bond to the carbon atom to which $R_2$ and $R_3$ are attached is conveniently attached meta to X and para to the ring nitrogen, respectively. X is conveniently sulphur, imino or lower alkylamino. $R_1$ is preferably a radical of formula IIb, IIc or IId or especially IIa. $R_2$ is preferably hydrogen. $R_3$ is preferably hydrogen and $R_4$ is conveniently alkyl. $R_5$ is conveniently hydrogen. $R_6$, when it is a heterocycle, conveniently contains one oxygen or sulphur atom or one or two nitrogen atoms. Preferably the bond linking $R_6$ to the vinylene moiety is attached to a ring carbon atom adjacent to a ring heteroatom. Conveniently the ring is unsubstituted or substituted by lower alkyl. $R_{10}$ is conveniently phenylalkoxy. IIa is conveniently optionally substituted 2 or 4pyridyl. In IIIc, IIId, IIIe it is to be appreciated that the bond linking $R_6$ to the vinylene moiety and $R_{11}$ to $R_{13}$ may be attached to any of the ring carbon atoms present. IIIc is preferably a cycloalk-1-en-1-yl radical. Preferably $R_{11}$ to $R_{13}$ are hydrogen. q is conveniently 0 or 1. Any double bond in IIIf is conveniently trans. $R_{14}$ is conveniently alkoxy ($C_{1-8}$) carbonyl, phenyl or alkyl or phenalkyl. $R_{17}$ is conveniently halogen and $R_{18}$ is conveniently hydrogen. $R_6$ is conveniently IIIc. u is conveniently 3, 4 or 5, more conveniently 4.

The values m, n, p, q, s, t and v are conveniently chosen to produce a five or six-membered ring.

The double bond between $R_6$ and the nitrogen atom preferably has the trans configuration.

Halogen is conveniently fluorine, or preferably bromine or chlorine.

When $R_1$ is IIb or IIe and $R_6$ is IIIa it is to be appreciated that the two radicals $R_9$ may be the same or different.

The present invention also provides a process for the production of a compound of formula I, which comprises
(a) reacting a compound of formula IV,

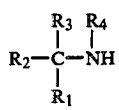
IV wherein
$R_1$ to $R_4$ are as defined above, with a compound of formula V,

V wherein
A is a leaving group, and
$R_5$ and $R_6$ are as defined above, or
(b) producing a compound of formula Ia,

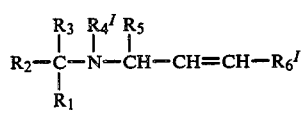
Ia wherein
$R_1$ to $R_3$ and $R_5$ are as defined above, and
$R_4^I$ and $R_6^I$ are as defined above for $R_4$ and $R_6$ respectively, with the proviso that they each are other than alkynyl,
by reducing a compound of formula VI,

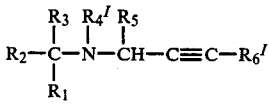

VI wherein
$R_1$ to $R_3$, $R_4^I$, $R_5$ and $R_6^I$ are defined above,
or
(c) producing a compound of formula Ib,

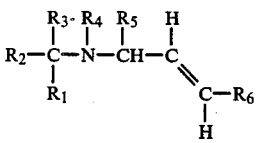

Ib wherein
$R_1$ to $R_6$ are as defined above,
by isomerising photochemically a compound of formula Ic,

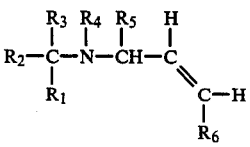

Ic wherein
$R_1$ to $R_6$ are as defined above, or
(d) producing a compound of formula Id,

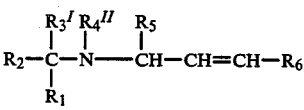

Id wherein
$R_1$, $R_2$, $R_5$ and $R_6$ are as defined above,
$R_3^I$ is hydrogen or lower alkyl,
$R_4^{II}$ is alkyl ($C_{1-6}$), alkenyl ($C_{3-12}$), alkynyl ($C_{3-12}$) or cycloalkyl ($C_{3-8}$) alkyl ($C_{1-6}$);
by introducing the group $R_4^{II}$ into a compound of formula VII,

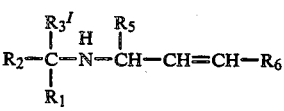

VII wherein
$R_1$, $R_2$, $R_3^I$, $R_5$ and $R_6$ are as defined above.

Process (a) may be effected in conventional manner for the production of tertiary amines by condensation from analogous starting materials. The process may be effected in an inert solvent such as a lower alkanol, e.g. ethanol, optionally in aqueous admixture, an aromatic hydrocarbon solvent, e.g. benzene or toluene, a cyclic ether, e.g. dioxane or a carboxylic acid dialkylamide solvent, e.g. dimethylformamide. The reaction temperature is conveniently from room temperature to the boiling temperature of the reaction mixture, preferably room temperature. The reaction is conveniently effected in the presence of an acid binding agent, such as an alkali metal carbonate, e.g. sodium carbonate. The leaving group A is conveniently iodine or preferably chlorine or bromine, or an organic sulphonyloxy group having 1 to 10 carbon atoms, e.g. alkylsulphonyloxy, preferably having 1 to 4 carbon atoms such as mesyloxy, or alkylphenylsulphonyloxy preferably having 7 to 10 carbon atoms such as tosyloxy.

Process (b) may be effected in conventional manner for catalytic hydrogenation in order to produce a compound of formula Ia wherein the double bond adjacent to $R_6^I$ has the cis configuration. Alternatively, the process may be effected in conventional manner for a complex metal hydride reduction in order to produce a compound of formula Ia wherein the double bond has the trans configuration.

The catalytic hydrogenation may be effected in a solvent, e.g. methanol, ethanol, methylene chloride, pyridine or ethyl acetate. The catalyst is preferably palladium on a carrier material such as $BaSO_4$ or $CaCO_3$. The catalyst may be pretreated, e.g. with a lead salt, so as to be partially poisoned (e.g. a Lindlar catalyst). The hydrogenation may be effected at room temperature and at normal pressure.

The metal hydride reduction may be effected in conventional manner for a lithium aluminium hydride or a diisobutylaluminium hydride reduction. The reduction is conveniently effected in an inert solvent such as toluene or benzene. The reaction is conveniently effected at room temperature.

Process (c) may be effected in conventional manner for a photochemical isomerisation of a cis alkene. The reaction may be effected in a solvent such as benzene, petroleum ether, ethanol, or preferably cyclohexane. The solution is conveniently irradiated with light from a mercury high or low pressure lamp. The reaction is conveniently effected at room temperature. If desired, an appropriate sensitizer such as eosine or a catalyst such as diphenyldisulphide may be present.

Process (d) may be effected in manner conventional for the "alkylation" of secondary amines (the term "alkylation" being used here to denote introduction of any of the hydrocarbyl groups $R_4^{II}$), for example by direct "alkylation" with an "alkylating" agent, for example a halide or sulphate, or by reductive alkylation, in particular by reaction with an appropriate aldehyde and subsequent or simultaneous reduction. Reductive "alkylation" is suitably effected in an inert organic solvent, such as a lower alkanol, e.g. methanol, and at an elevated temperature, in particular at the boiling temperature of the reaction medium. The subsequent reduction may be effected with, for example, a complex metal hydride reducing agent, e.g. $NaBH_4$ or $LiAlH_4$. The reduction may also be effected simultaneously to the alkylation, for example by use of formic acid which may serve both as reducing agent and as a reaction medium.

It is to be appreciated that in any of the above processes, side reactions may occur, e.g. reduction of halogen to hydrogen, reduction of a nitro group to an amino group, reduction of an alkenyl moiety to an alkyl moiety and/or reduction of a keto moiety to a carbinol moiety in processes (b) or process (d) when reductive alkylation is used, or simultaneous cis/trans isomerisation of any double bond present in $R_4$ or $R_6$ when process (c) is used. The reaction conditions should be chosen to avoid such side reactions, and the desired final product isolated using conventional purification techniques, e.g. thin layer chromatography.

Free base forms of the compounds of formula I may be converted into salt forms and vice versa. Suitable acids for acid addition salt formation include hydrochloric acid, fumaric acid and naphthalene-1,5-disulphonic acid.

The starting materials are either known or may be made in conventional manner. For example non-cyclic amines of formula IV may be made by condensing a compound of formula VIII, $$R_2-\underset{R_1}{\underset{|}{\overset{R_3{}^I}{\overset{|}{C}}}}-Br \quad \text{VIII}$$

or the corresponding iodide or chloride, with a compound of formula $R_4{}^{II}NH_2$.

The cyclic amines of formula IV may be made as follows:

$$R_1MgBr + \underset{\text{IX}}{\underset{OCH_3}{\left(\!\!\begin{array}{c}(CH_2)_u\\ \\ \phantom{x}=N\end{array}\!\!\right)}} \longrightarrow \underset{X}{R_1-\overset{(CH_2)_u}{\underset{}{C=N}}}$$

$$\underset{XI}{R_1-C=N} \xrightarrow[\text{or NaBH}_4]{\text{Alk MgBr}} IV$$

wherein
Alk = lower alkyl.

The compounds of formula VI are new and may be made by reacting an appropriate amine of formula IV with compounds of formulae $R_5$—CHO and HC≡$CR_6{}^I$ under Mannich reaction conditions.

The compounds of formula VII are also new and may be made as follows:

$$R_2-\underset{R_1}{\underset{|}{\overset{R_3{}^I}{\overset{|}{C}}}}-NH_2 + \underset{O}{\overset{R_5}{\underset{\|}{\overset{|}{C}}}}-CH=CH-R_6 \longrightarrow$$

$$R_2-\underset{R_1}{\underset{|}{\overset{R_3{}^I}{\overset{|}{C}}}}-N=\overset{R_5}{\underset{}{\overset{|}{C}}}-CH=CH-R_6 \xrightarrow{NaBH_4} VII$$

In the following Examples all temperatures are uncorrected and in degrees Centigrade.

In the tables hereinafter, the following indications are used:
(1) All double bonds have the trans configuration; all alkyl groups are unbranched unless stated otherwise.
(2) If no melting point is given, the free base form of the compound is obtained and this is an oil. Melting points are for the free base form unless specified otherwise.
(3) Monohydrochloride salt form.
(4) Dihydrochloride salt form.

EXAMPLE 1

4-[N-methyl-N-(1-naphthylmethyl)]aminocrotonic acid ethyl ester [process (a)]

1.9 g of bromocrotonic acid ethyl ester are added dropwise to a mixture of 1.7 g of N-methyl-N-(1-naphthylmethyl)amine, 1.4 g of $K_2CO_3$ and 10 ml dimethylformamide. After the mixture is stirred for 18 hours at room temperature, it is filtered and evaporated under a vacuum. The residue is chromatographed on silica-gel using benzene/ethyl acetate (1:1) as solvent to yield the title compound in free base form, as an oil, after evaporating the appropriate fractions.

The title compound may also be made in analogous manner to Examples 3, 4 and 5.

EXAMPLE 2

N-(3-cyclohex-1en-1yl-2-cis-propenyl)-N-methyl-N-(1-naphthylmethyl)amine [process (b)]

5 g of N-(3cyclohex-1-en-1-yl-propynyl)-N-methyl-N-(1-naphthylmethyl)amine are hydrogenated in absolute pyridine using 750 mg Pd/BaSO$_4$ as catalyst at room temperature and normal pressure, until the calculated amount of hydrogen is taken up. The reaction mixture is filtered and the pyridine removed in a vacuum. The residue is chromatographed on silica-gel using benzene/ethylacetate (9:1) to yield the title compound in free base form as an oil after evaoporating the appropriate fractions,
m.p. (hydrochloride) 184°–188°.

The title compound may also be made in analogous manner to Examples 1 and 5.

EXAMPLE 3

N-(3-cyclohexyl-2-trans-propenyl)-N-methyl-N-(1-naphthylmetyl)amine [process (b)]

28 ml of a 1.2 molar solution of diisobutylaluminium hydride in toluene are added to 5 g of N-(3-cyclohexyl-propynyl)-N-methyl-N-(1-naphthlmethyl)amine in absolute benzene. After the mixture is stirred for 3 hours at 40°, water is carefully added. The organic phase is separated off, dried and evaporated to yield the title compound in free base form, as an oil.

The title compound may also be prepared by following Examples 1, 4 and 5.

EXAMPLE 4

N-(3-cyclohex-1-en-1-yl-2-trans-propenyl)-N-methyl-N-(1-naphthylmethyl)amine [process (c)]1.2 g of N-(3-cyclohex-1-en-1-yl-2-cis-propenyl)-N-methyl-N-(1-naphthylmethyl)amine are irradiated for 3 hours with a Hg high pressure lamp (λ>300 nm) in 1 liter cyclohexane in the presence of 50 mg diphenyldisulphide at room temperature under an inert gas atmosphere. After the solvent is evaporated, the title compound is obtained in free base form and converted into the hydrochloride, m.p. 184°–188°

The title compound may also be prepared by following Examples 1, 3 and 5.

EXAMPLE 5

N-methyl-N-[3-(5'-methyl-2'-thienyl)-2-transpropenyl]-N-(1-naphthylmethyl)amine [process d)]

(a) 15.2 g of 3-(5'-methyl-2'-thienyl)prop-2-enal and 15.7 g of 1-aminomethylnaphthalene in 350 ml benzene are boiled under reflux until the calculated amount of water has boiled off. 3.6 g of the resulting Schiff base in 100 ml methanol are boiled under reflux with 5 g NaBH₄ for 30 minutes to yield N-[3-(5'-methyl-2'-thienyl)-2-trans-propenyl)]-N-(1-naphthylmethyl)amine, which is used directly in the next stage. [To isolate this intermediate the reaction mixture is evaporated in a vacuum; the residue is partitioned between aqueous sodium carbonate solution and diethyl ether and the organic phase is evaporated].

(b) The crude reaction mixture obtained in step a) is treated with 20 ml 37% aqueous formaldehyde solution. The mixture is boiled under reflux for 60 minutes, subjected to ice-cooling, treated with 9 g NaBH₄ and stirred for another 60 minutes at room temperature. The mixture is evaporated in a vacuum to a residue which is partitioned between aqueous NaHCO₃ and diethyl ether. The organic phase is dried and evaporated to yield the title compound in free base form as an oil, m.p. (hydrochloride) 140°–156°.

The title compound may also be prepared in analogous manner to Examples 1, 3 and 4.

In analogous manner to that described in Examples 1, 3, 4 and 5, the following trans compounds of formula Ie may be produced:

$$R_1-CH_2-N(CH_3)-CH_2-CH=CHR_6 \quad \text{Ie}$$

wherein $R_1$ and $R_6$ are as follows:

| Ex. | $R_1$ | $R_6^1$ | m.p.² |
|---|---|---|---|
| 6 | 1-naphthyl | —COOC₅H₁₁ | |
| 7 | 1-naphthyl | —COOC₈H₁₇ | |
| 8 | 1-naphthyl | —COOCH₂C₆H₅ | |
| 9 | 1-naphthyl | 2-thienyl | 182–187³ |
| 10 | 1-naphthyl | 2-furyl | |
| 11 | 1-naphthyl | 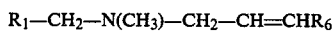 | 175–185⁴ |
| 12 | 1-naphthyl | Cyclohex-3-en-1-yl | |
| 13 | 1-naphthyl | 2-pyridyl | |
| 14 | 1-naphthyl | 3-pyridyl | |
| 15 | 1-naphthyl | 4-pyridyl | 174–178⁴ |
| 16 | 1-naphthyl | —CH=CH.C₆H₅ | 170–174³ |
| 17 | 1-naphthyl | —CH=CH.C₄H₉ | |
| 18 | 1-naphthyl | 2-pyrrolyl | |
| 19 | 1-naphthyl | Cyclohept-1-en-1-yl | 193–196³ |
| 20 | 1-naphthyl | Cyclopent-1-en-1-yl | |
| 21 | 1-naphthyl | 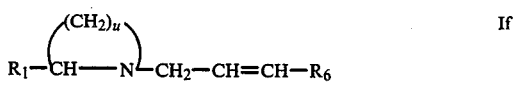 | 180–184³ |
| 22 | 1-naphthyl | —CH=CH—COOC₂H₅ | |
| 23 | 1-tetralinyl | C₆H₅ | |
| 24 | 1-tetralinyl | Cyclohex-1-en-1-yl | |
| 25 | 5-tetralinyl | C₆H₅ | |
| 26 | 4-quinolyl | C₆H₅ | |
| 27 | 3-benzo[b]thienyl | C₆H₅ | |
| 28 | 3-benzo[b]thienyl | Cyclohex-1-en-1-yl | 175–177³ |

-continued

| Ex. | $R_1$ | $R_6^1$ | m.p.² |
|---|---|---|---|
| 29 | 1-naphthyl | (1,2-dimethylcyclohex-1-en-1-yl structure) | |
| 30 | 1-naphthyl | (N-ethyl-2,5-dihydropyrrol-2-yl structure) | |
| 31 | 1-naphthyl | (1-methyl-3-phenylindol-2-yl structure) | |

In analogous manner to that described above for Examples 1, 3 and 4 there may be produced the following trans compounds of formula If, $$R_1-\underset{\underset{(CH_2)_u}{\diagup\diagdown}}{CH}-N-CH_2-CH=CH-R_6 \quad \text{If}$$

wherein $R_1$, $R_6$ and u are as follows:

| Ex. | $R_1$ | $R_6^1$ | u | m.p.² |
|---|---|---|---|---|
| 32 | 1-naphthyl | C₆H₅ | 4 | 203–205³ |
| 33 | 1-naphthyl | C₆H₅ | 3 | 75–78 |
| 34 | 1-naphthyl | C₆H₅ | 5 | 171–175³ |
| 35 | 1-naphthyl | COOC₅H₁₁ | 4 | |
| 36 | 1-naphthyl | C₆H₅ | 1 | |
| 37 | 1-naphthyl | Cyclohex-1-en-1-yl | 4 | |
| 38 | 1-naphthyl | 4-F-C₆H₄ | 4 | |
| 39 | 1-naphthyl | 3-pyridyl | 4 | |
| 40 | 3-benzo[b]thienyl | C₆H₅ | 4 | |
| 41 | 5-tetralinyl | C₆H₅ | 4 | 150–155³ |

EXAMPLE 42

In analogous manner to that described in Examples 1 and 2, the following cis compound of formula I may be produced:
(aa)   N-(3-cyclohex-1-en-1-yl-2-cis-propenyl)-2-(1'-naphthyl)piperidine; free base-oil.

EXAMPLES 43–47

In analogous manner to that described in Examples 1, 3, 4 and 5, the following compounds of formula I may be produced:
(43)   N-cinnamyl-N-methyl-N-[2-(1'-naphthyl)-2-propyl]amine; free base-oil;
(44)   N-(1-acenaphthenyl)-N-methyl-N-(3-phenyl-2-transpropenyl)amine, m.p. (hydrochloride) 210°–216°;
(45) N-(1-acenaphthenyl)-N-methyl-N-[3-(5'-methyl-2'-thienyl)-2-trans-propenyl)amine, free base-oil;
(46) N-(6,7,8,8a-tetrahydro-1-acenaphthenyl)-N-methyl-N-(3-phenyl-2-trans-propenyl)amine, m.p. (hydrochloride) 185°–192°;

(47) N-methyl-N-(2,3-dihydro-1-phenalenyl)-N-(3-phenyl-2-trans-propenyl amine), free base-oil.

NMR data on the above-mentioned compounds of formula I, obtained as oils, are given in the following table. The data comprises peak position in ppm relative to TMS as standard in $CDCl_3$; type of peak (D=doublet; DD=double doublet; DT=double triplet; M=multiplet; Q=quartet; S=singlet; T=triplet) and in parentheses the corresponding number of hydrogen atoms.

| Ex. | NMR Data |
|---|---|
| 1 | 1.2 T (3); 2.25 S (3); 3.2 M (2); 3.9 S (2); 4.2 Q (2); 6.0 D (1); 6.85–7.2 M (1); 7.3–7.9 M (6); 8.2 (1). |
| 3 | 0.8–2.2 (11); 2.2 S (3); 3.0 M (2); 3.85 S (2); 5.6 M (2); 7.3–7.9 (6); 8.3 M (1) |
| 6 | 0.7–1.8 M (9); 2.25 S (3); 3.2 M (2); 3.9 S (2) 4.1 T (2); 6.0 D (1); 6.9–7.2 M (1); 7.3–7.9 M (6); 8.3 M (1); 4.1 T (2). |
| 7 | 0.8–1.8 M (15); 2.3 S (3); 3.25 M (2); 3.95 S (1); 4.1 T (2); 6.0 M (1); 6.9–7.2 M (1); 7.4–7.9 M (6); 8.2–8.4 M (1) |
| 8 | 2.3 S (3); 3.2 M (2); 3.9 S (2); 5.15 S (2); 6.1 M (1); 6.9–7.9 M (13); 8.2–8.4 M (1). |
| 10 | 2.28 S (3); 3.28 T (2); 3.94 S (2); 6.25 M (4); 7.42 M |
| 12 | 1–2.5 M (7); 2.2 S (3); 3.0 M (2); 3.85 S (2); 6.4–6.8 M (4); 7.2–7.9 (6); 8.2–8.4 M (1). |
| 13 | 2.3 S (3); 3.35 D (2); 4.0 S (2); 7.0–8.0 M (9); 8.2–8.4 M (1); 8.55 M (1) |
| 14 | 2.3 S (3); 3.25 D (2); 3.95 S (2); 6.2–6.7 M (2); 7.0–7.8 M (8); 8.2–8.7 M (3) |
| 17 | 0.8–1.5 (7); 3.0–3.3 M (2); 3.2 S (3); 3.15 D (2); 3.9 S (2); 5.5–6.4 M (4); 7.2–8.4 (7). |
| 18 | 2.26 S (3); 3.22 D (2); 3.94 S (2); 5.85 DT; 6.18 M (2); 6.45 D (1); 6.74 M (1); 7.4–8.5 M (6); 8.3 M (1) |
| 20 | 1.7–2.1 (2); 2.2–2.6 (4); 2.2 S (3); 3.15 D (2); 3.86 S (2); 5.5–5.85 M (2); 6.45 D (1); 7.2–7.9 (6); 8.3 M (1). |
| 22 | 1.28 T (3); 2.24 S (3); 3.2 D (2); 3.9 S (2); 4.2 Q (2); 5.84 D (1); 6.2–6.5 M (2); 7.2–7.9 (7); 8.2–8.3 M (1) |
| 23 | 1.6–1.9 M (4); 2.2 S (3); 2.7–2.9 M (4); 3.2 D (2); 3.45 S (2); 6.1–6.7 M (2); 6.9–7.5 (8) |
| 24 | 1.4–1.9 (8); 2.0–2.3 (4); 2.17 S (3); 2.8 M (4); 3.06 D (2); 3.4 S (2); 5.4–5.8 (2); 6.16 D (1); 6.9–7.2 (4) |
| 25 | 1.6–2.1 M (4); 2.35 S (3); 2.2–3.4 M (7); 6.0–6.6 M (2); 7.0–7.4 M (9) |
| 26 | 2.3 S (3); 3.25 D (2); 3.9 S (2); 6.2–6.7 M (2); 7.1–7.8 (9); 8.2 M (2); 8.85 D (1) |
| 27 | 2.3 S (3); 3.25 D (2); 3.8 S (2); 6.2–6.7 M (2); 7.2–7.5 (8); 7.8–8.0 M (2) |
| 29 | 1.1 D (3); 1.3–2.8 (7); 1.75 S (3); 2.25 S (3); 3.25 D (2); 3.91 M (2); 5.8 DT (1) 6.5 D (1); 7.3–7.9 (6); 8.3 M (1) |
| 30 | 1.33 T (3); 2.27 S (3); 3.26 D (2); 3.91 Q (2); 3.94 S (2); 6.0–6.7 M (5); 7.3–7.7 M (4); 7.7–7.9 M (2); 8.3 M (1); |
| 31 | 2.28 S (3); 3.02 S (3); 3.18 D (2); 3.86 S (2); 6.2–6.6 M (2); 6.65 (1); 7.0–7.4 M (8); 8.0 M (1) |
| 35 | 2.5–2.8 DD (1); 3.1–3.5 M (3); 3.8–4.0 M (1) 4.1 T (2); 5.9 D (1); 6.7–7.05 M (1); 7.3–8.0 M (6); 8.5 M (1) |
| 36 | 1.9–2.1 M (2); 2.95–3.1 M (1); 3.4 D (1); 6.2–6.8 M (2); 7.0–8.4 (12); |
| 37 | 2.4–2.7 DD (1); 3.0–3.5 M (3); 3.7–4.0 (1); 5.2–5.6 M (3); 5.9 D (J = 16 Hz) (1); 7.3–8.0 (6); 8.3–8.8 (1) |
| 38 | 1.3–2.4 M (7); 2.65 DD (1); 3.15–3.25 M (2); 3.65–3.95 (1); 5.8–6.4 (2); 6.8–7.9 (10); 8.3–8.8 broad S (1) |
| 39 | 1.2–2.8 (8); 3.15–3.45 (2); 3.8–4.0 (1); 6.2 M (2); 7.0–7.9 (8); 8.2–8.6 (3); |
| 40 | 1.2–2.4 (7); 2.6–2.85 DD; 3.15–3.8 (3); 6.1–6.8 (2); 7.1–7.6 (8); 7.8–7.9 M (1); 8.15–8.25 M (1) |
| 42 | 2.8–3.1 DD (1); 3.1–3.5 M (3); 3.7–4.0 (1); 5.2–5.6 M (3); 5.8 D (J = 13 Hz) (1); 7.3–8.0 (6); 8.3–8.8 (1) |
| 43 | 1.62 S (6); 2.34 S (3); 3.15 D (2); 6.03 DT (1); 6.40 D (1); 7.1–7.9 (11); 9.55 M (1) |
| 45 | 2.18 S (3); 2.40 S (3); 3.20 M (4); 4.95 M (1); 6.50 M; 7.10 M |
| 47 | 2.38 S (3); 3.30 M (4); 4.20 M (1); 6.35 M (2); 7.30 M (11) |

In analogous manner to that described in Example 1, the following compounds of formula I may be produced, wherein $R_2$=n-butyl, either $R_3$=n-butyl and $R_4$=cyclooctyl-methyl, cyclopropylhexyl, allyl, dodec-2-ynyl, or $R_3+R_4=-(CH_2)_8-$ $R_5$=n-butyl, the double bond is cis, and $R_1$ and $R_6$ as follows:

| Ex. | $R_1$ | $R_6$ |
|---|---|---|
| (a) | 6-bromo-2-fluoronaphthalenyl | CH₃–C(NH)=N–CH=CH– (methyl amidino vinyl) |
| (b) | 6-(trifluoromethyl)-3-ethoxynaphthalenyl | 5-methoxy-2-thienyl |

-continued

| Ex. | $R_1$ | $R_6$ |
|---|---|---|
| (c) | 8-hydroxy-5-iodo-1-naphthyl (methyl-substituted) | 2-hydroxy-pyrrol-5-yl (NH) |
| (d) | 8-ethyl-5-nitro-1-naphthyl (methyl-substituted) | 3-bromo-5-methyl-thien-2-yl |
| (e) | 8-ethoxy-1-naphthyl (methyl-substituted) | 3-ethyl-pyridin-4-yl |
| (f) | 2-methyl-benzofuran-3-yl | 4-ethoxy-pyridin-3-yl |
| (g) | 3-ethyl-4-methyl-indol-2-yl (NH) | 2-hydroxy-pyridin-3-yl |
| (h) | 2-hydroxymethyl-5-methyl-benzofuran-3-yl | 4-bromo-pyridin-2-yl |
| (i) | 2-ethoxy-4-methyl-6-(propenyl/propyl) substituted phenyl | $-CO \cdot C_{10}H_{21}$ |
| (j) | 2-bromo-7-methyl-benzofuran-3-yl | $COO \cdot CH_2 \cdot CH=CH_2$ |

-continued

| Ex. | R₁ | R₆ |
|---|---|---|
| (k) | 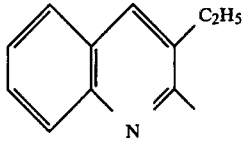 (quinoline with C₂H₅ and CH₃ substituents) | COO.CH₂.C≡C.C₇H₁₅ |
| (l) | 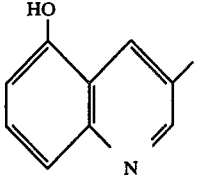 (5-hydroxy-3-methylquinoline) | —CO.[CH₂]₆-▷ |
| (m) | 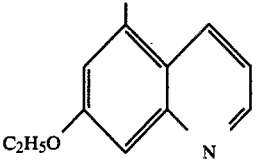 (quinoline with CH₃ and C₂H₅O substituents) | CO.O.CH₂.Cyclooctyl |
| (n) | 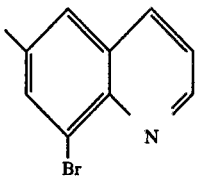 (quinoline with CH₃ and Br substituents) | CO.[CH₂]₅.C₆H₅ |
| (o) | 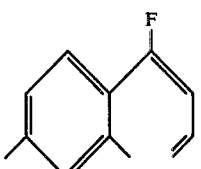 (quinoline with F and CH₃ substituents) | CO.C₆H₅ |
| (p) | 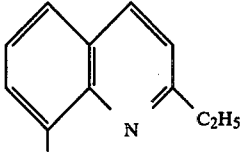 (quinoline with CH₃ and C₂H₅ substituents) | CO.C₆H₅ |
| (q) | 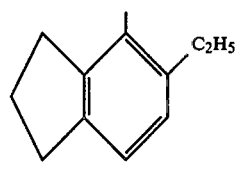 (indane with CH₃ and C₂H₅ substituents) | CO.(CH₂)₁₀.NH₂ |
| (r) | 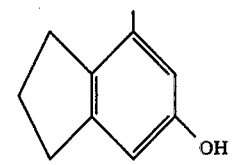 (indane with CH₃ and OH substituents) | ▭ |

-continued

| Ex. | R₁ | R₆ |
|---|---|---|
| (s) | 4-ethoxy-5-indanyl (indane with OC₂H₅) | $CH_3-C(=CH-)-(CH_2)_3-CH(C_2H_5)-CH(C_2H_5)-C_2H_5$ (branched alkenyl with three C₂H₅ groups) |
| (t) | 2-bromo-indanyl | cyclopentadienyl |
| (u) | 1-indanyl | cyclohexenyl with two C₂H₅ on double bond and (CH₂)₃ bridge |
| (v) | 6-ethyl-benzocycloheptyl | cyclopropyl |
| (w) | 5-hydroxy-1-indanyl | cycloheptyl with three C₂H₅ substituents |
| (x) | 6-ethoxy-1-indanyl | all cis-$(C(C_2H_5)=C(C_3H_7))_5-CH_2.CH=CH.C_5H_{11}$ |
| (y) | 8-bromo-1-indanyl | all trans-$(CH=CH)_3-CH_2.C{\equiv}CH$ |
| (z) | 8-bromo-1-indanyl | all trans-$(CH=CH)_4-CH_2.C_6H_5$ |

In analogous manner to that described in Example 1, the following compounds of formula I may be produced wherein
$R_3$=n-butyl
$R_5$=n-butyl
the double bond is cis, and
$R_1+R_2$ together with the carbon atom to which they are bound is

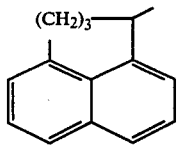

and R₆ is as follows:

| Ex. | R₆ |
|---|---|
| (i) | 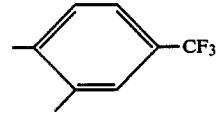 |
| (ii) | 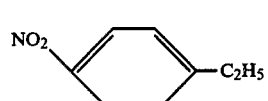 |
| (iii) | 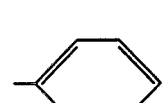 |

The compounds of formula I are useful because they possess chemotherapeutic activity. In particular, they are useful as antimycotic agents, as indicated with in vitro tests against various families and types of mycetes, including Trichophton quinkeanum, Aspergillus fumigatus, Microsporum canis, Sporotrychium schenkii and Candida albicans, at concentrations of, for example 0.1 to 100 μg/ml. An experimental skin mycosis model in guinea pigs is used for in vivo tests. The guinea pigs are infected by cutaneous application of Trichophyton quinkeanum. The test substance is administered daily for 7 days beginning 24 hours after the infection by local application by rubbing the test substance (taken up in polyethylene glycol) on the skin surface, or perorally as a suspension for 9 days beginning on the day of infection. The activity is shown on local application at concentrations of for example 0.1 to 2%, in particular 0.1 to 0.6%. The oral activity is shown at dosages of, for example, 50 to 100 mg/kg.

For the above-mentioned use, the dose administered will of course vary depending on the compound employed, mode of administration and treatment desired. However, in general, satisfactory results are obtained when administered at a daily dosage of from 10 to 100 mg/kg of animal body weight, conveniently given in divided doses two to four times daily, or in sustained release form. For the larger mammals, the corresponding daily dosages are in the range of from 500 to 2000 mg, and dosage forms suitable for oral administration comprise from 125 to 1000 mg.

The compounds may be used in free base form or in the form of chemotherapeutically acceptable acid addition salts. Such salt forms exhibit the same order of activity as the free base forms.

The compounds may be admixed with conventional chemotherapeutically acceptable diluents and carriers, and, optionally, other excipients and administered in such forms as tablets or capsules. The compounds may alternatively be administered topically in such conventional forms as ointments or creams. The concentration of the active substance in such topical application forms will of course vary depending on the compound employed, the treatment desired and the nature of the form etc. In general, however, satisfactory results are obtained at concentrations of from 0.05 to 3, in particular 0.1 to 1 wt %.

A compound with particularly interesting activity is the compound of Example 4.

One group of compounds has a formula Ig,

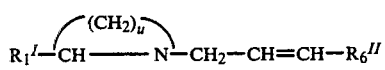

Ig wherein
$R_1{}^I$ is 1-naphthyl, optionally mono-substituted by lower alkyl or alkoxy,
u is a whole number from 1 to 8,
$R_6{}^{II}$ is of formula

 (a)

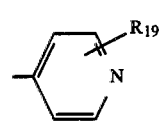 (b)

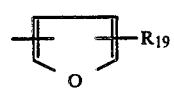 (c)

 (d)

wherein $R_{19}$ is hydrogen, hydroxy, lower alkoxy or lower alkyl,
or of formula $-CO-OR_{20}$ (e)

wherein $R_{20}$ is alkyl ($C_{1-12}$) or phenylalkyl($C_{7-12}$) or of formula

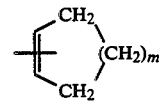 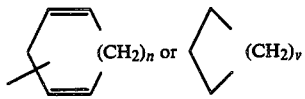

(f) (g) (h)

wherein m, n and v are as defined above.

Another group of compounds comprises those of formula Ih,

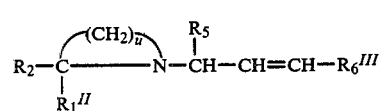

Ih wherein $R_1{}^{II}$ is a radical of formula IIa, IIb wherein X is oxygen or sulphur, IIc, IId wherein s is 4, IIe wherein t is 3 or a radical of formula

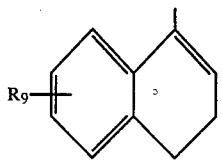

wherein $R_9$ is as defined above,
$R_2$ and $R_5$ are independently hydrogen or lower alkyl,
u is a whole number from 1 to 8,
$R_6{}^{III}$ is as defined above for $R_6$, with the following provisos,
(a) $R_{10}$ is other than phenyl or phenylalkoxy, and
(b) when $R_1{}^{II}$ is 1-naphthyl optionally mono-substituted by lower alkyl or alkoxy and $R_2$ and $R_5$ are each hydrogen, $R_6{}^{III}$ is other than
  (i) a radical of formula IIIa, IIIb or IIIf,
  (ii) a radical of formula IIIc, IIId or IIIe, wherein $R_{11}$, $R_{12}$ and $R_{13}$ are each hydrogen, or
  (iii) a radical of formula IIIg wherein one of $R_{17}$ and $R_{18}$ is hydrogen and the other is hydroxy, lower alkyl or lower alkoxy, or
  (iv) an optionally substituted thiophen or furan radical.

A further group of formula I compounds comprises compounds of formula Ii,

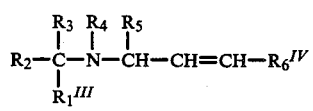

wherein
$R_1{}^{III}$ is a radical of formula IIa, IIb wherein X is oxygen or sulphur, IIc, IId wherein s is 4, IIe wherein t is 3, or a radical of formula

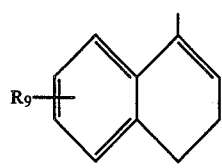

$R_2$, $R_3$, $R_4$, $R_5$ and $R_9$ are as defined above, with the proviso that $R_3$ and $R_4$ are other than —(CH$_2$)$_u$—,
$R_6{}^{IV}$ is as defined above for $R_6$ with respect to formula I, with the following provisos
(i) $R_{10}$ is other than phenyl or phenylalkoxy and
(ii) when $R_1$ is a radical of formula IIa, $R_6{}^{IV}$ is other than a radical of formula IIIg, or phenyl.

In a first group of compounds $R_1$ is a radical of formula IIa.

In a second group of compounds $R_1$ is a radical of formula IIb. In a 1st sub-group X is O; in a 2nd sub-group X is S; in a 3rd sub-group X is imino; in a 4th sub-group X is lower alkyl amino; in a 5th sub-group X is —CH$_2$—. In a 6th sub-group X is —CH$_2$—CH$_2$—. In a 7th sub-group X is —CH$_2$—CH$_2$—CH$_2$.

In a third group of compounds $R_1$ is a radical of formula IIc.

In a fourth group of compounds $R_1$ is a radical of formula IId.

In a fifth group of compounds $R_1$ is a radical of formula IIe.

In a sixth group of compounds $R_1$ together with $R_2$ and the carbon atom to which they are bound are a radical of formula IIg.

In a 7th group of compounds $R_1$ together with $R_2$ and the carbon atom to which they are bound are a radical of formula IIh.

In an 8th group of compounds $R_4$ is alkyl.
In a 9th group of compounds $R_4$ is alkenyl.
In a 10th group of compounds $R_4$ is alkynyl.
In an 11th group of compounds $R_4$ is cycloalkylalkyl.
In a 12th group of compounds $R_6$ is a heterocycle. In a 1st sub-group $R_6$ is pyrroyl; in a 2nd sub-group $R_6$ is furyl; in a 3rd sub-group $R_6$ is thienyl; in a fourth sub-group $R_6$ is imidazoyl.

In a 13th group of compounds $R_6$ is a radical of formula IIIa.

In a 14th group of compounds $R_6$ is a radical of formula IIIb. In a first sub-group $R_{10}$ is alkyl; in a 2nd sub-group $R_{10}$ is alkenyl; in a 3rd sub-group $R_{10}$ is alkynyl: in a 4th sub-group $R_{10}$ is cycloalkylalkyl; in a 5th sub-group $R_{10}$ is phenylalkyl; in a 6th sub-group $R_{10}$ is phenyl; in a 7th sub-group $R_{10}$ is phenylalkoxy; in an 8th sub-group $R_{10}$ is aminoalkyl.

In a 15th group $R_6$ is a radical of formula IIIc.
In a 16th group $R_6$ is a radical of formula IIId.
In a 17th group $R_6$ is a radical of formula IIIe.
In an 18th group $R_6$ is a radical of formula IIIf. In a 1st sub-group q is 0; in a 2nd sub-group q is 1; in a 3rd sub-group $R_{14}$ is alkyl; in a 4th sub-group $R_{14}$ is alkoxycarbonyl; in a 5th sub-group $R_{14}$ is alkenyl; in a 6th sub-group $R_{14}$ is alkynyl; in a 7th sub-group $R_{14}$ is phenylalkyl; in an 8th sub-group $R_{14}$ is phenyl.

In a 19th group $R_6$ is a radical of formula IIIg.

In a 20th group $R_3$ and $R_4$ together are —(CH$_2$)$_u$—. In a 1st sub-group u is 1; in a 2nd sub-group u is 4; in a 5th sub-group u is 5; in a 6th sub-group u is 6; in a 7th sub-group u is 7; in an 8th sub-group u is 8.

We claim:
1. A compound of formula I,

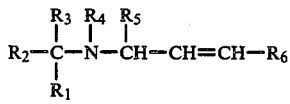

wherein
(a)
(i) $R_1$ is a radical of formula IIa,

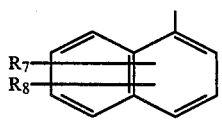

wherein
$R_7$ and $R_8$, independently, are hydrogen, halogen of atomic number from 9 to 53, trifluoromethyl, hydroxy, nitro, lower alkyl or lower alkoxy, or a radical of formula IIb, IIc, IId, IIe,

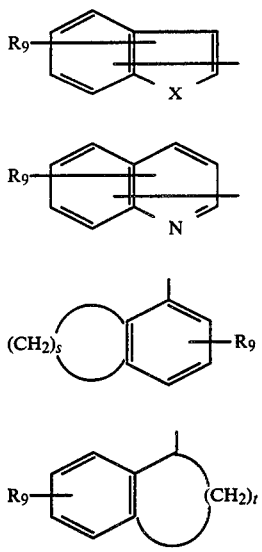 IIb

IIc

IId

IIe wherein
R$_9$ is hydrogen, halogen of atomic number from 9 to 53, hydroxy, lower alkyl or lower alkoxy,
X is oxygen, sulphur, imino, lower alkylimino or a radical of formula —(CH$_2$)$_r$— wherein r is 1, 2 or 3,
s is 3, 4 or 5, and
t is 2, 3 or 4, and
R$_2$ is hydrogen or lower alkyl, or
(ii) R$_1$ and R$_2$ together with the carbon atom to which they are bound form a radical of formula IIf or IIg,

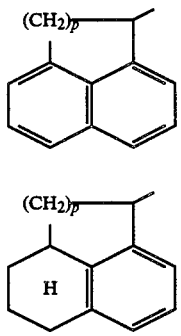 IIf

IIg wherein
p is 1, 2 or 3,
R$_3$ and R$_5$, independently, are hydrogen or lower alkyl,
R$_4$ is alkyl (C$_{1-6}$), alkenyl (C$_{3-12}$), alkynyl (C$_{3-12}$) or cycloalkyl (C$_{3-8}$)alkyl (C$_{1-6}$); and
R$_6$ is (i) an aromatic, five-membered heterocycle containing one oxygen, sulphur or nitrogen hetero-ring atom and optionally an additional one or two nitrogen hetero-ring atoms and being optionally substituted on a carbon ring atom by halogen of atomic number from 9 to 53, hydroxy, lower alkyl or lower alkoxy, and any nitrogen ring atom present being optionally substituted when possible, by lower alkyl, (ii) a radical of formula IIIa,

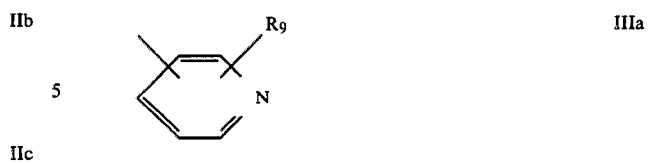 IIIa wherein
R$_9$ is as defined above,
(iii) a radical of formula IIIb,

—CO—R$_{10}$   IIIb wherein
R$_{10}$ is alkyl (C$_{1-12}$), alkenyl (C$_{3-12}$), alkynyl (C$_{3-12}$) cycloalkyl (C$_{3-8}$)alkyl (C$_{1-6}$), phenyl-alkyl (C$_{7-12}$), phenyl, phenylalkoxy (C$_{7-16}$), or aminoalkyl (C$_{1-12}$);
(iv) a radical of formula IIIc, IIId or IIIe,

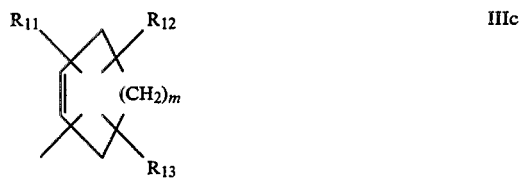 IIIc

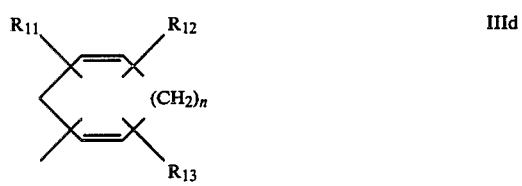 IIId

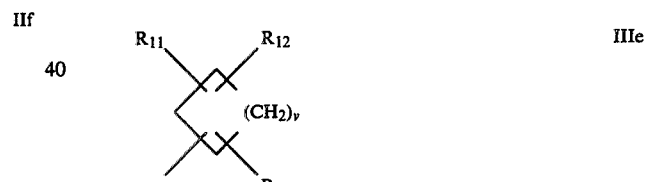 IIIe wherein
R$_{11}$, R$_{12}$ and R$_{13}$, independently, are hydrogen or lower alkyl,
m is a whole number from 0 to 4,
n is a whole number from 0 to 3, and
v is a whole number from 0 to 5,
(v) a radical of formula IIIf,

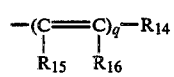

wherein
R$_{14}$ is lower alkyl, alkoxy (C$_{1-12}$)carbonyl, alkenyl (C$_{3-12}$), alkynyl (C$_{3-12}$), phenylalkyl (C$_{7-12}$) or phenyl,
R$_{15}$ and R$_{16}$, independently, are hydrogen or lower alkyl, and
q is a whole number from 0 to 5, or
(vi) a radical of formula IIIg

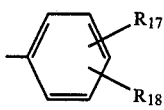 IIIg wherein $R_{17}$ and $R_{18}$, independently, are hydrogen, halogen of atomic number from 9 to 53, trifluoromethyl, hydroxy, nitro, lower alkyl or lower alkoxy, with the general proviso that $R_1$ is not a radical of formula IIa when $R_6$ is a radical of formula IIIg or phenyl or phenylalkyl, (b)
$R_1$ is a radical of formula IIa to IIe, as defined above,
$R_2$, $R_5$ and $R_6$ are as defined above, and
$R_3$ and $R_4$ together are $-(CH_2)_u-$ wherein u is a whole number from 1 to 8.

or a chemotherapeutically acceptable salt thereof.

2. A pharmaceutical composition which comprises a therapeutically effective amount of a compound of claim 1, in association with a chemotherapeutically acceptable diluent or carrier.

3. A compound of claim 1, having the formula Ig,

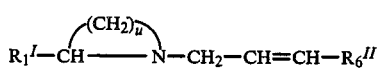 Ig wherein $R_1{}^I$ is 1-naphthyl, optionally mono-substituted by lower alkyl or alkoxy,
u is a whole number from 1 to 8,
$R_6{}^{II}$ is of formula

 (a)

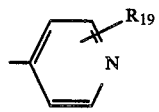 (b)

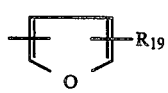 (c)

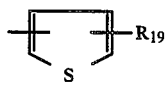 (d)

wherein
$R_{19}$ is hydrogen, hydroxy, lower alkoxy or lower alkyl,
or of formula $-CO-OR_{20}$ (e)

wherein
$R_{20}$ is alkyl ($C_{1-12}$) or phenylalkyl($C_{7-12}$)
or of formula

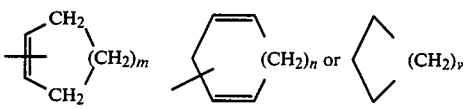

(f) (g) (h)

wherein
m, n and v are as defined in claim 1.

4. A compound of claim 1, having the formula Ih,

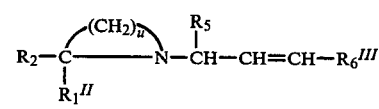 Ih wherein
$R_1{}^{II}$ is a radical of formula IIa, IIb wherein X is oxygen or sulphur, IIc, IId wherein s is 4, IIe wherein t is 3 or a radical of formula

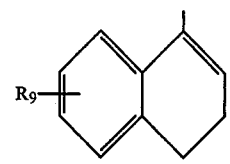

wherein
$R_9$ is as defined in claim 1,
$R_2$ and R are independently hydrogen or lower alkyl,
u is a whole number from 1 to 8,
$R_6{}^{III}$ is as defined in claim 1 for $R_6$, with the following provisos,
  (a) $R_{10}$ is other than phenyl or phenylalkoxy, and
  (b) when $R_1{}^{II}$ is 1-naphthyl optionally mono-substituted by lower alkyl or alkoxy and $R_2$ and $R_5$ are each hydrogen, $R_6{}^{III}$ is other than
    (i) a radical of formula IIIa, IIIb or IIIf,
    (ii) a radical of formula IIIc, IIId or IIIe, wherein $R_{11}$, $R_{12}$ and $R_{13}$ are each hydrogen, or
    (iii) a radical of formula IIIg wherein one of $R_{17}$ and $R_{18}$ is hydrogen and the other is hydroxy, lower alkyl or lower alkoxy, or
    (iv) an optionally substituted thiophen or furan radical.

5. A compound of claim 1 having the formula Ii,

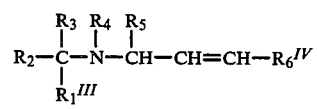 Ii wherein
$R_1{}^{III}$ is a radical of formula IIa, IIb wherein
X is oxygen or sulphur, IIc, IId wherein a is 4, IIe wherein t is 3, or a radical of formula

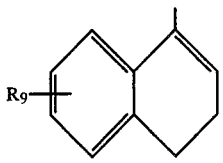

$R_2$, $R_3$, $R_4$, $R_5$ and $R_9$ are as defined in claim 1, with the proviso that $R_3$ and $R_4$ are other than —(CH$_2$)$_u$—, $R_6^{IV}$ is as defined in claim 1 for $R_6$ with respect to formula I, with the following provisos
(i) $R_{10}$ is other than phenyl or phenylalkoxy and
(ii) when $R_1$ is a radical of formula IIa, $R_6^{IV}$ is other than a radical of formula IIIg, or phenyl.

6. A compound of claim 1, which is N-(3-cyclohex-1-en-1-yl-2-trans-propenyl)-N-methyl-N-(1-naphthylmethyl)amine.

7. A method of combatting mycoses in or on animals which comprises administering an anti-mycotic amount of a compound of claim 1 to an animal in need of such treatment.

8. The compound according to claim 1 which is 4-[N-methyl-N-(1-naphthylmethyl)]aminocrotonic acid ethyl ester.

9. The compound according to claim 1 which is N-(3-cyclohex-1-en-1-yl-2-cis-propenyl)-N-methyl-N-(1-naphthylmethyl)amine.

10. The compound according to claim 1 which is N-(3-cyclohexyl-2-trans-propenyl)-N-methyl-N-(1-naphthylmethyl)amine.

11. The compound according to claim 1 which is N-methyl-N-[3-(5'-methyl-2'-thienyl)-2-trans-propenyl)-N-(1-naphthylmethyl)amine.

12. A compound according to claim 1 of the formula Ie:

$$R_1-CH_2-N(CH_3)-CH_2-CH=CHR_6 \qquad \text{Ie}$$

in which $R_1$ and $R_6$ are as defined in claim 1.

13. The compound of claim 12 in which $R_1$ is 1-naphthyl and $R_6$ is 2-thienyl.

14. The compound according to claim 12 in which $R_1$ is 1-naphthyl and $R_6$ is

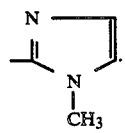

15. The compound according to claim 12 in which $R_1$ is 1-naphthyl and $R_6$ is 4-pyridyl.

16. The compound according to claim 12 in which $R_1$ is 1-naphthyl and $R_6$ is —CH=CH.C$_6$H$_5$.

17. The compound according to claim 12 in which $R_1$ is 1-naphthyl and $R_6$ is Cyclohept-1-en-1-yl.

18. The compound according to claim 12 in which $R_1$ is 1-naphthyl and $R_6$ is

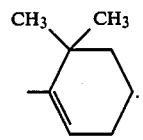

19. The compound according to claim 12 in which $R_1$ is 3-benzo[b]thienyl and $R_6$ is Cyclohex-1-en-1-yl.

20. A compound according to claim 1 of the formula If:

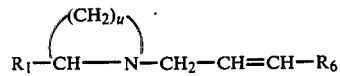

in which $R_1$, $R_6$ and u are as defined in claim 1.

21. The compound of claim 20 in which $R_1$ is 1-naphthyl, $R_6$ is C$_6$H$_5$ and u is 4.

22. The compound of claim 20 in which $R_1$ is 1-naphthyl, $R_6$ is C$_6$H$_5$ and u is 3.

23. The compound of claim 20 in which $R_1$ is 1-naphthyl, $R_6$ is C$_6$H$_5$ and u is 5.

24. The compound of claim 20 in which $R_1$ is 5-tetralinyl $R_6$ is C$_6$H$_5$ and u is 4.

25. The compound of claim 1 which is N-(3-cyclohex-1-en-1-yl-2-cis-propenyl)-2-(1'-naphthyl)-piperidine.

26. The compound of claim 1 which is N-(1-acenaphthenyl)-N-methyl-N-(3-phenyl-2-trans-propenyl)amine.

27. The compound of claim 1 which is N-(1-acenaphthenyl)N-methyl-N-[3-(5'-methyl-2'-thienyl)-2-trans-propenyl]amine.

28. The compound of claim 1 which is N-(6,7,8,8a-tetrahydro-1-acenaphthenyl)-N-methyl-N-(3-phenyl-2-transpropenyl)amine.

29. The compound of claim 1 which is N-methyl-N-(2,3-dihydro-1-phenalenyl)-N-(3-phenyl-2-trans-propenyl)amine.

30. A compound according to claim 1 in which $R_6$ is an aromatic, five membered heterocycle as defined in claim 1.

31. A compound according to claim 1 in which $R_6$ is a radical of formula IIIa.

32. A compound according to claim 1 in which $R_6$ is a radical of formula IIIb.

33. A compound according to claim 1 in which $R_6$ is a radical of the formula IIIc, IIId or IIIe.

34. A compound according to claim 1 in which $R_6$ is a radical of the formula IIIf.

35. A compound according to claim 3 in which $R_{14}$ is alkoxycarbonyl, alkenyl, alkynyl or phenylalkyl.

36. A compound according to claim 1 in which $R_3$ and $R_4$ together are –(CH$_2$)$_u$ wherein u is a whole number from 1 to 8; $R_1$ is a radical of Formula IIa to IIe and $R_2$, $R_5$ and $R_6$ are as defined in claim 1.

37. A compound according to claim 1 of the formula:

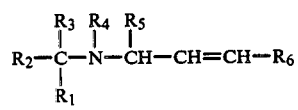

wherein
$R_1$ is a radical of formula IIa,

wherein $R_7$ and $R_8$, independently, are hydrogen, halogen of atomic number from 9 to 53, trifluoromethyl, hydroxy, nitro, lower alkyl or lower alkoxy, or a radical of formula IIb, IIc, IId, IIe,

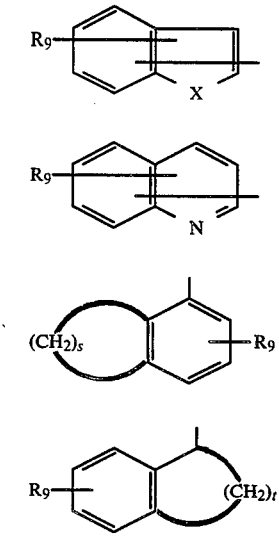

IIb

IIc

IId

IIe wherein
$R_9$ is hydrogen, halogen of atomic number from 9 to 53, hydroxy, lower alkyl or lower alkoxy,
X is oxygen, sulphur, imino, lower alkylimino or a radical of formula —$(CH_2)_r$—
wherein r is 1, 2 or 3,
s is 3, 4 or 5, and
t is 2, 3 or 4, and
$R_2$ is hydrogen or lower alkyl, or
$R_3$ and $R_5$, independently, are hydrogen or lower alkyl,
$R_4$ is alkyl ($C_{1-6}$), alkenyl ($C_{3-12}$), alkynyl ($C_{3-12}$) or cycloalkyl ($C_{3-8}$) alkyl($C_{1-6}$); and
$R_6$ is
(i) an aromatic, five-membered heterocycle containing one oxygen, sulphur or nitrogen hetero-ring atom and optionally an additional one or two nitrogen hetero-ring atoms and being optionally substituted on a carbon ring atom by halogen of atomic number from 9 to 53, hydroxy, lower alkyl or lower alkoxy, and any nitrogen ring atom present being optionally substituted when possible, by lower alkyl,
(ii) a radical of formula IIIa,

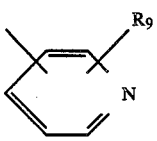

IIIa wherein
$R_9$ is as defined above,
(iii) a radical of formula IIIb,

—CO—$R_{10}$  IIb wherein
$R_{10}$ is alkyl ($C_{1-12}$), alkenyl($C_{3-12}$), alkynyl ($C_{3-12}$) cycloalkyl ($C_{3-8}$)alkyl ($C_{1-6}$), phenyl-alkyl ($C_{7-12}$), phenyl, phenylalkoxy ($C_{7-16}$), or aminoalkyl ($C_{1-12}$);
(iv) a radical of formula IIIc, IIId or IIIe,

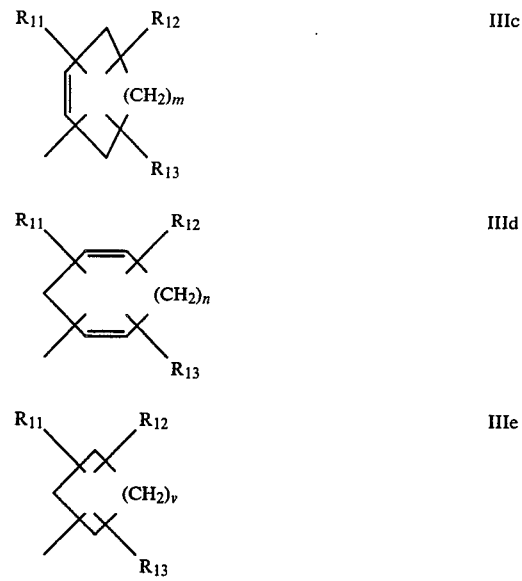

IIIc

IIId

IIIe wherein
$R_{11}$, $R_{12}$ and $R_{13}$, independently, are hydrogen or lower alkyl,
m is a whole number from 0 to 4,
n is a whole number from 0 to 3, and
v is a whole number from 0 to 5, or (v) a radical of formula IIIf, $-(C=C)_q-R_{14}$
  $|\ \ |$
  $R_{15}\ R_{16}$ IIIf wherein
$R_{14}$ is lower alkyl, alkoxy ($C_{1-12}$)carbonyl, alkenyl ($C_{3-12}$), or alkynyl($C_{3-12}$),
$R_{15}$ and $R_{16}$, independently, are hydrogen or lower alkyl, and
q is a whole number from 0 to 5,
or a chemotherapeutically acceptable salt thereof.

38. A compound according to claim 37 in which $R_1$ is

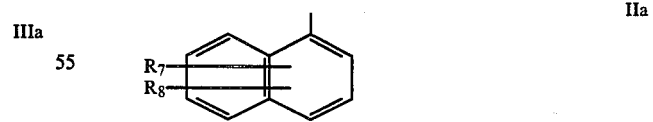

IIa and $R_6$ is

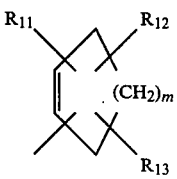

IIIc

-continued

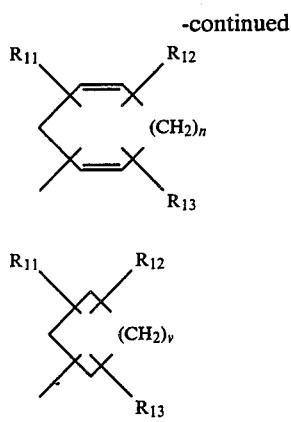

IIId

IIIe where m, n, v, $R_7$, $R_8$, $R_{11}$, $R_{12}$ and $R_{13}$ are as defined in claim 37.

39. A compound according to claim 37 in which $R_1$ is

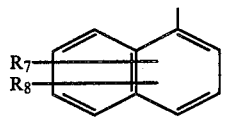

IIa and $R_6$ is

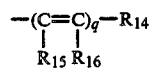

IIIf and q, $R_7$, $R_8$, $R_{14}$, $R_{15}$ and $R_{16}$ are as defined in claim 37.

40. A compound according to claim 37 in which q is 0 or 1.

41. A compound according to claim 1 in which $R_1$ is

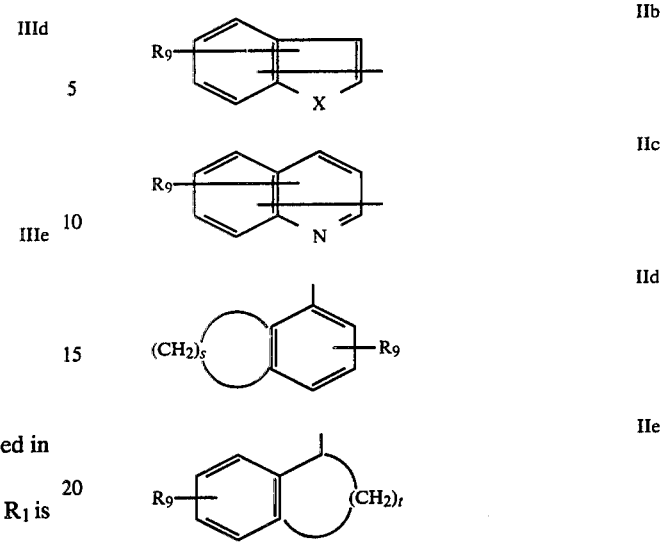

and s, t, X and $R_9$ are as defined in claim 1.

42. A compound according to claim 1 in which $R_1$ and $R_2$ together with the carbon atom to which they are bound form a radical of formula IIf or IIg,

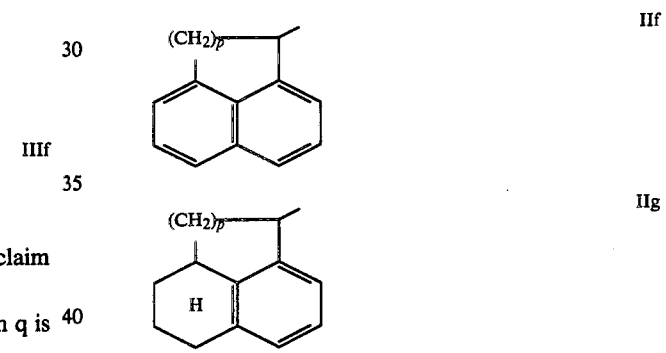

wherein p is 1, 2 or 3.

* * * * *